US009335245B2

(12) United States Patent  (10) Patent No.: US 9,335,245 B2
Song et al.  (45) Date of Patent: May 10, 2016

(54) METHOD OF REDUCING UNCERTAINTY IN PRESSURE PULSE-DECAY MEASUREMENT

(71) Applicant: KOREA INSTITUTE OF GEOSCIENCE AND MINERAL RESOURCES, Daejeon (KR)

(72) Inventors: In-Sun Song, Daejeon (KR); Jeong-Chan Kim, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 234 days.

(21) Appl. No.: 14/023,200

(22) Filed: Sep. 10, 2013

(65)  Prior Publication Data

US 2014/0069183 A1  Mar. 13, 2014

(30)  Foreign Application Priority Data

Sep. 11, 2012  (KR) .................. 10-2012-0100488

(51) Int. Cl.
*G01N 15/08*  (2006.01)
(52) U.S. Cl.
CPC ............ *G01N 15/08* (2013.01); *G01N 15/0826* (2013.01)
(58) Field of Classification Search
CPC .. G01N 15/08; G01N 15/082; G01N 15/0826
See application file for complete search history.

(56)  References Cited

U.S. PATENT DOCUMENTS 4,506,542 A * 3/1985 Rose .................................. 73/38
4,552,011 A * 11/1985 Wiley ............................. 73/1.69
4,571,985 A * 2/1986 Daly ................................. 73/38
5,417,104 A * 5/1995 Wong ................................ 73/38
5,813,798 A * 9/1998 Whiffen .................... B09C 1/00
       210/739

(Continued)

FOREIGN PATENT DOCUMENTS

CN      2188205 Y      1/1995
CN    201532351 U      7/2010

(Continued)

OTHER PUBLICATIONS

JP 2000081378 A—Original.*

(Continued)

*Primary Examiner* — Lisa Caputo
*Assistant Examiner* — Tran M Tran
(74) *Attorney, Agent, or Firm* — Lewis Roca Rothgerber Christie LLP

(57)  ABSTRACT

A method of reducing uncertainty, which exactly finds the hydraulic conductivity and the specific storativity of a rock sample in pressure pulse-decay measurement. Axial and confining pressures are applied to the rock sample, and upstream and downstream reservoirs are connected to the rock sample. Coordinate values representing minimum values of a contour of a graph of an objective function, in which the hydraulic conductivity and the specific storativity obtained through the pressure pulse-decay measurement scheme to apply pressure pulses from the outside are expressed in horizontal and vertical axes are found from the graph. The coordinate values are set as the hydraulic conductivity and the specific storativity of the rock sample. Graphs of objective functions obtained by repeating the pressure pulse-decay measurement while changing boundary conditions are shown in overlapped, thereby reducing the uncertainty of the hydraulic conductivity and the specific storativity of the rock sample.

10 Claims, 4 Drawing Sheets

(56) References Cited

U.S. PATENT DOCUMENTS

| | | | |
|---|---|---|---|
| 6,178,808 B1 * | 1/2001 | Wang et al. | 73/38 |
| 6,321,317 B1 * | 11/2001 | Borowsky | G06F 9/5016 |
| | | | 711/158 |
| 6,415,648 B1 * | 7/2002 | Peeters | 73/38 |
| 6,986,281 B1 * | 1/2006 | Hubbell et al. | 73/152.01 |
| 7,254,564 B2 * | 8/2007 | Coppola, Jr. | G01V 9/02 |
| | | | 703/10 |
| 7,882,726 B2 * | 2/2011 | Gupta et al. | 73/38 |
| 8,806,954 B1 * | 8/2014 | Hubbell | 73/861 |
| 2008/0000666 A1 | 1/2008 | Keskiniva et al. | |
| 2010/0089124 A1 * | 4/2010 | Katti et al. | 73/38 |
| 2011/0067857 A1 * | 3/2011 | Underhill | E21B 43/26 |
| | | | 166/250.01 |

FOREIGN PATENT DOCUMENTS

| | | | | |
|---|---|---|---|---|
| JP | 2000-009631 A | | 1/2000 | |
| JP | 2000-081378 A | | 3/2000 | |
| JP | 2000081378 A | * | 3/2000 | G01N 3/00 |
| JP | 2008-514832 | | 5/2008 | |

OTHER PUBLICATIONS

Translation of JP 2000081378 A.*

Wang et al., "Experimental Error for Permeability and Specific Storage from Pulse Decay Measurements", 1993, Int. J. Rock Mech. Min. Sci. & Geomech, vol. 30, No. 7, pp. 1173-1176.*

Zhang et al., "Evaluation and Application of the Transient-Pulse Technique for Determining the Hydraulic Properties of Low-Permeability Rocks—Part 2: Experimental Application", 2000, American Society for Testing and Materials.*

Tokunaga et al. "Determination of Hydraulic Conductivity and Storage Coefficient Through Simultaneous Measurements of Fluid Pressure and Strains", Jour. Japan Soc. Eng. Geol., vol. 42, No. 4, pp. 208-213, 2001, English translation of abstract only, 6 pages.

Chinese Office action along with English Translation for Patent Application No. 201310410037.7, dated Sep. 29, 2014, 15 pages.

Brace, et al., "Permeability of Granite under High Pressure," Journal of Geophysical Research, vol. 73, No. 6, Mar. 13, 1968, pp. 2225-2236.

Hsieh, et al., "A Transient Laboratory Method for Determining the Hydraulic Properties of 'Tight' Rocks—I. Theory," Int. J. Rock Mech. Min. Sci. & Geomech. Abstr., vol. 18, 1981, pp. 245-252.

Wang, et al., "Experimental Error for Permeability and Specific Storage from Pulse Decay Measurements," Int. J. Rock Mech. Min. Sci. Geomech. Abstr., vol. 30, No. 7, 1993, pp. 1173-1176.

Zhang, et al., "Evaluation and Application of the Transient-Pulse Technique for Determining the Hydraulic Properties of Low-Permeability Rocks—Part 2: Experimental Application," Geotechnical Testing Journal, vol. 23, No. 1, Mar. 2000, pp. 91-99.

* cited by examiner

US 9,335,245 B2

METHOD OF REDUCING UNCERTAINTY IN PRESSURE PULSE-DECAY MEASUREMENT

CROSS-REFERENCE TO RELATED APPLICATION

This application claims the benefit under 35 U.S.C. §119 of Korean Patent Application No. 10-2012-0100488 filed on Sep. 11, 2012 in the Korean Intellectual Property Office, the entirety of which disclosure is incorporated herein by reference.

BACKGROUND OF THE INVENTION

1. Field of the Invention

The present invention relates to a method of reducing the uncertainty when measuring the hydraulic conductivity and the specific storativity of a rock sample.

2. Description of the Related Art

In order to prevent the contamination of various landfills from being spread when underground water resources or petroleum resources are developed, in order to investigate an underground bedrock environment, or in order to perform other various civil engineering works, site investigations are required. Among them, representatively, the measurement of the permeability or storativity of bedrock is required.

In this case, the permeability of the bedrock refers to the easy liquidity of a fluid flowing through fluid passages communicating with each other through gaps in the bedrock. Since the flow of the fluid through the fluid passage receives the resistance by attraction force or pressure, permeability may be represented differently depending on bedrocks or stratums.

In addition, the storativity of bedrock refers to the characteristics of the bedrock related to the storage capacity of a fluid when injecting the fluid through fluid passages communicating with each other through the gaps in the bedrock. If the potential energy or the kinetic energy is not changed, the fluid does not flow, but is maintained in a stationary state.

In general, when a fluid (representatively, water) inflows into or outflows from an underground rock formation or a stratum (hereinafter, collectively, rock formation), the diffusion of the pressure of the fluid may be affected by the permeability or the storativity of rocks mainly constituting a bedrock or a related stratum.

In this case, the permeability or the storativity of the bedrock is an essentially required parameter to estimate the inflow/outflow place of the fluid or estimate the variation (diffusion) of the fluid according to the elapse of time.

Since the permeability or the storativity of the rock formation is a characteristic generated in an underground natural state, the real permeability or storativity of the rock formation cannot be actually detected. Accordingly, generally, required data are acquired through a hydraulic test in a laboratory.

The permeability or the storativity may be measured through various schemes. When rocks constituting the rock formation are densely formed and have impermeability, a pulse-decay (transient) scheme is used to apply pressure pulses to a rock sample for the measurement in order to reduce the measurement time.

As representative values having the numerical characteristics of a rock sample constituting a target rock formation through the hydraulic test in the above laboratory, hydraulic conductivity and the storage coefficient can be calculated.

In this case, the hydraulic conductivity is defined as the passing speed of water, that is, a value obtained by dividing a passing distance of water by time. As the value of the hydraulic conductivity is reduced, the flow of the fluid (water) is more difficult in the underground rock formation.

In addition, the storage coefficient is defined as the quantity of water per area inflowing into or outflowing from an aquifer due to the variation of the unit hydraulic head.

Meanwhile, the specific storativity (specific storage) is defined as the quantity (volume) of water inflowing into or outflowing from the aquifer due to the increase or the drop of the unit hydraulic head per unit volume in the aquifer. If the thickness of the aquifer is multiplied by the specific storativity, the storage coefficient can be found.

According to the pulse-decay scheme of the related art, only the hydraulic conductivity is measured under the assumption that the specific storativity is 0, or the hydraulic conductivity and the specific storativity are calculated by inversely calculating the pressure curve.

However, the first problem in the scheme of obtaining the hydraulic conductivity and the specific storativity according to the related art is that the degree of the uncertainty of each parameter is not provided.

In other words, since an experimental error essentially exists in the pressure measured in the hydraulic test of a laboratory, both of the hydraulic conductivity and the specific storativity inevitably have a slight degree of uncertainty. However, according to the related art, since data related to the uncertainty are not provided, the reliability of the experiment cannot be recognized.

The second problem is that the uncertainty of a parameter resulting from the experimental error is varied depending on an experimental system (the sizes of the upper and downstream reservoirs; see reference numerals 10 and 20 of FIG. 1 in relation to the upper and downstream reservoirs). In this case, the condition used to find the parameter cannot be recognized.

The third problem is that the uncertainties of parameters are affected by each other according to the conditions of the hydraulic test. If the uncertainty of any one parameter is unknown, the uncertainty of another parameter is not recognized.

The scheme of finding the hydraulic conductivity and the specific storativity according to the related art does not provide solutions to the above problems.

Meanwhile, there are following non-patent documents (papers) as documents of the related art.

(1) Brace, W. F., J. B. Walsh, and W. T. Frangos, Permeability of granite under high pressure, J. Geophys. Res. 1968 73 2225-2236.

(2) Hsieh, P. A., J. V. Tracy, C. E. Neuzil, J. D. Bredehoeft, and S. E. Silliman, A transient laboratory method for determining the hydraulic properties of tight bedrocks-I. Theory, Int. J. Bedrock Mech. Min. Sci. & Geomech. Abstr. 1981 18 245-252.

(3) Wang, H. F., and D. J. Hart, Experimental error for permeability and specific storage from pulse decay measurements, Int. J. Mech. Min. Sci. Geomech. Abstr. 1993 30, 1173-1176.

(4) Zhang, M., M. Takahashi, R. H. Morin, and T. Esaki, Evaluation and application of the transient-pulse technique for determining the hydraulic properties of low-permeability bedrocks-Part 2: Experimental application, Geotechnical Testing Journal 2000b; 23, 091-099.

SUMMARY OF THE INVENTION

The prevent invention has been made in an effort to solve the above-described problems, and an object of the present invention is to improve the reliability of an experiment by clearly providing data related to the uncertainty of each parameter.

In addition, another object of the present invention is to clearly detect the uncertainties of parameters resulting from the experimental error by finding conditions used to calculate the parameters.

Further, still another object of the present invention is to clearly detect the uncertainties of parameters even if the uncertainties of the parameters are affected by each other.

In order to accomplish the above objects, there is provided a method of reducing an uncertainty in pressure pulse-decay measurement. The method includes placing a rock sample inside a sleeve in a housing, fixing the rock sample by mounting end plugs and porous disks on left and right sides of the rock sample, respectively, connecting upstream and downstream reservoirs to the porous disks of the fixed rock sample axially outward of the porous disks, attaching pressure gauges to the upper and downstream reservoirs, respectively, applying an axial pressure and a confining pressure to the rock sample placed in the sleeve to form a closed pressure system, applying a pressure pulse to the rock sample in the closed pressure system through the upstream reservoir, and finding a hydraulic conductivity and a specific storativity based on variation of the pressure pulse obtained when the pressure pulse is decayed.

In this case, the finding of the hydraulic conductivity and the specific storativity may include obtaining coordinates representing a minimum value of a contour in a graph of an objective function, which represents a sum of differences between calculated values of the hydraulic conductivity and the hydraulic conductivity and variation measurement values of the pressure pulse obtained from the pressure gauge, or an average value thereof, from the graph and setting the minimum values as the hydraulic conductivity and the specific storativity of the rock sample.

In addition, preferably, the sleeve includes a rubber.

In addition, the applying of the axial pressure and the confining pressure to the rock sample may be performed by supplying a fluid to a fluid inflow space.

Preferably, the fluid to apply the confining pressure and the axial pressure is oil.

According to another aspect of the present invention, there is provided a method of reducing an uncertainty in pressure pulse-decay measurement. The method includes placing a rock sample inside a sleeve in a housing, fixing the rock sample by mounting end plugs and porous disks on left and right sides of the rock sample, respectively, connecting upstream and downstream reservoirs to the fixed rock sample, attaching pressure gauges to the upper and lower reservoirs, respectively, placing two valves, which are spaced apart from each other, to adjust a size of the upstream reservoir, applying an axial pressure and a confining pressure to the rock sample placed in the sleeve to form a closed pressure system, applying a pressure pulse to the rock sample in the closed pressure system through the upper reservoir, and finding a hydraulic conductivity and a specific storativity based on variation of the pressure pulse obtained when the pressure pulse is decayed.

In this case, preferably, the finding of the hydraulic conductivity and the specific storativity includes obtaining coordinates representing a minimum value of a contour in a graph of an objective function, which represents a sum of differences between calculated values of the hydraulic conductivity and the hydraulic conductivity and variation measurement values of the pressure pulse obtained from the pressure gauge, or an average value thereof, from the graph and setting the minimum values as the hydraulic conductivity and the specific storativity of the rock sample.

Preferably, the applying of the pressure pulse includes applying the pressure pulse through the upstream reservoir in a state that the size of the upstream reservoir is adjusted by controlling the two valves spaced apart from each other.

In this case, uncertainties of the hydraulic conductivity and the specific storativity of the rock sample may be reduced by expressing graphs of objective functions obtained by repeating the applying of the pressure pulse several times through overlap of the graphs.

In addition, preferably, the sleeve includes a rubber.

Further, the applying of the axial pressure and the confining pressure to the rock sample may include supplying a fluid to a fluid inflow space.

Preferably, the fluid to apply the confining pressure and the axial pressure is oil.

As described above, according to the present invention, since the uncertainties of parameters resulting from the experimental error can be provided, the reliability of the experiment can be evaluated.

In addition, according to the present invention, since the experimental conditions are clearly provided, a simple simulation can be performed before an experiment is performed. Accordingly, the optimal experimental system can be designed. Therefore, the uncertainties of parameters can be reduced by providing boundary conditions in which the uncertainties are not affected by each other.

In addition, according to the present invention, even if uncertainties are not affected by each other between parameters during the hydraulic test, since the uncertainty of one of parameters may be limited through another experiment, the more exact result of the hydraulic test can be obtained.

DETAILED DESCRIPTION OF THE INVENTION

The advantages, the features, and schemes of achieving the advantages and features of the present invention will be apparently comprehended by those skilled in the art based on the embodiments, which are detailed later in detail, together with accompanying drawings. The present invention is not limited to the following embodiments but includes various applications and modifications. The embodiments will make the disclosure of the present invention complete, and allow those skilled in the art to completely comprehend the scope of the present invention. The present invention is only defined within the scope of accompanying claims.

Hereinafter, a method of reducing uncertainty in pressure pulse-decay measurement according to a preferred embodiment of the present invention will be described in detail with reference to accompanying drawings.

First, the structure of a hydraulic testing device used in the method of reducing uncertainty in pressure pulse-decay measurement according to the present invention will be described.

Figure 1:
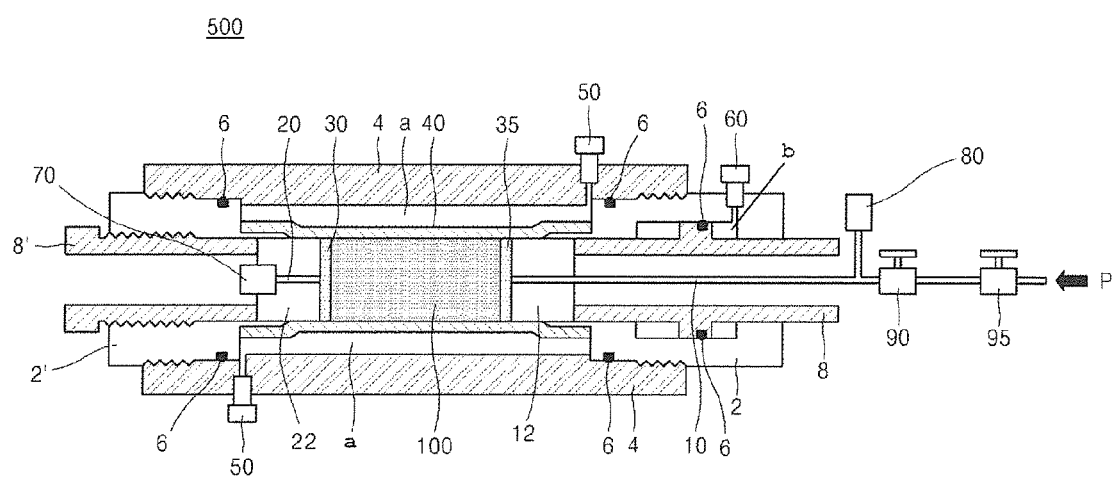
FIG. 1 is a sectional view schematically showing a 3-axis-core holder device used in pressure pulse-decay measurement according to the present invention in order to measure the hydraulic conductivity and the specific storativity of a rock sample.

FIG. 1 is a sectional view schematically showing a 3-axis-core holder device 500.

The 3-axis-core holder device 500 is mainly divided into an upper part, a body part, and a lower part. In drawings, the left side represents the lower part, and the right side represents the upper part.

A rock sample 100 used in the pressure pulse-decay measurement according to the present invention is provided inside a sleeve 40 of a housing 4 in the 3-axis-core holder device 500. As shown in FIG. 1, preferably, both sides of the sleeve 40 are spread to form the shape of a cylinder.

The sleeve 40 preferably includes a rubber material. However, the sleeve 40 may include other materials if the sleeve 40 has a structure in which a confining pressure can be properly delivered to the rock sample 100 when the confining pressure described below is applied to the sleeve 40.

The rock sample 100 is primarily fixed in the sleeve 40 of the body part in the sequence of an upper end plug 12 and a lower end plug 22 provided in an axial direction. The rock sample 100 is secondarily fixed to a top surface of the upper end plug 12 and a bottom surface of the lower end plug 22 axially outward of the upper and lower end plugs 12 and 22 by porous disks 30 and 35. Finally, the rock sample 100 is fixedly positioned by upper and lower holders 8 and 8' axially outward of the porous disks 30 and 35.

In this case, the axis direction refers to a right-left direction in drawings.

In addition, the upper end plug 12 and the lower end plug 22 preferably include stainless by taking into consideration the corrosion by a fluid or endurance.

At the upper part of the 3-axis-core holder device 500, an upstream reservoir 10 to which a pressure pulse P is delivered from the outside, an upper stream pressure gauge to measure the pressure pulse P in the upstream reservoir 10, and two valves 90 and 95 to adjust (control) the magnitude of the upstream reservoir 10 are provided while being spaced apart from each other by a proper distance.

In addition, the 3-axis-core holder device 500 is provided at the upper part thereof with the upper holder 8 to fix the upper end plug 12, which is used to fix the porous disk 35 outside the rock sample 100 in the body part, axially outward of the upper end plug 12, an upper holder supporting part 2 to surround the upper holder 8, and an upper fluid supply port 60 communicating with a space b between the upper holder 8 and the upper holder supporting part 2.

In this case, the positions of the upstream reservoir and the downstream reservoir 20 may be provided in opposition to each other. The two valves 90 and 95 may be installed to adjust the size of the downstream reservoir 20 instead of the size of the upstream reservoir 10.

In order to apply the axial pressure to the device 500, after placing the rock sample 100 in the body part, a fluid, preferably, oil having a predetermined viscosity is supplied to the fluid introducing space b through the upper fluid supply port 60, and the upper holder 8 is pushed to the left side of the drawings by the pressure of the supplied oil, so that the axial pressure may be applied to the rock sample 100.

In this case, an oil pressing part (not shown) is formed outside the upper fluid supply port 60 to press and supply oil.

The 3-axis-core holder device according to the present invention is provided at the body part thereof with the sleeve 40 having the rock sample 100 positioned therein, porous disks 30 and 35 to support both sides of the rock sample 100 in the sleeve 40, the upper and lower end plugs 12 and 22 to support the porous disks 30 and 35, respectively, a fluid inflow space a provided outside the sleeve 40, and body fluid supply ports 50 to supply a fluid to the fluid inflow space a to provide a confining pressure.

In this case, the oil used to form the confining pressure is preferably the same as oil used to form an axial pressure and having a predetermined viscosity. Similarly the upper fluid supply port 60, oil pressing parts (not shown) are preferably formed outside the body fluid supply ports 50.

The 3-axis-core holder device according to the present invention is provided at the lower part thereof with the downstream reservoir 20 having a structure corresponding to that of the upstream reservoir 10 provided at the upper part, a lower stream pressure gauge 70 attached to a lower end portion of the downstream reservoir 20 to measure the internal pressure of the device 500, the lower part holder 8' to fixedly maintain the lower end plug 22 axially formed outside a lower portion of the rock sample 100, and a lower part holder maintaining part 2' to surround the lower part holder 8'.

Although the communicating fluid inflow space b is formed between the upper part holder 8 and the upper holder supporting part 2 at the upper part of the device 500, a communication space is not formed between the lower part holder 8' and the lower part holder maintaining part 2' at the lower part.

Meanwhile, preferably, in the 3-axis-core holder device 500, fluid sealing o-rings 6 are provided in desirable numbers between the upper holder 8 and the upper holder supporting part 2, between the upper holder supporting part 2 and the housing 4, and between the housing 4 and the lower part holder maintaining part 2'.

In addition, the upper holder supporting part 2 and the housing 4, the housing 4 and the lower part holder maintaining part 2', and the lower part holder 8' and the lower part holder maintaining part 2' are preferably screw-coupled with each other. In particular, the screw-coupling between the lower part holder 8' and the lower part holder maintaining part 2' suitably adjusts the axial pressure of the fluid applied to the rock sample 100.

In other words, although the axial pressure may be formed by supplying a fluid from the upper fluid supply port 60 after positioning the rock sample 100 in the sleeve and finishing the device 500 as described above, the axial pressure can be finally adjusted through the screw-coupling between the lower part holder 8' and the lower part holder maintaining part 2' in order to form desirable axial pressure.

Hereinafter, the structure of the 3-axis-core holder device 500 according to the present invention to apply the confining pressure will be described.

After placing the rock sample 100 in the sleeve 40 and finishing the installation of the device 500, a fluid is supplied through the body fluid supply ports 50, and the supplied fluid pressurizes the sleeve 40 outward of the sleeve 40 in a concentric direction to provide the final confining pressure to the rock sample 100.

In this case, preferably, the confining pressure and the axial pressure are formed substantially simultaneously.

The fluid used to form the confining pressure is preferably oil the same as oil having a predetermined viscosity used to form the axial pressure. Similarly the upper fluid supply port 60, the oil pressing part (not shown) is formed outside the body fluid supply ports 50.

Hereinafter, the method of reducing the uncertainty in the pressure pulse-decay measurement according to the present invention will be described with reference to the constitution to fix the rock sample 100 to the 3-axis-core holder device 500 of FIG. 1 as described above.

After fixing the bedrock sample 100 to the 3-axis-core holder device 500, the upstream reservoir 10 and the downstream reservoir 20 are connected with both sides of the upper stream side and the lower stream side of the rock sample 100, and a pump (not shown) is connected with the upstream reservoir 10 to apply the pressure pulse P.

Thereafter, a closed pressure system is formed by applying the axial pressure and the confining pressure to the rock sample 100 as described above, and the pressure pulse P generated from the pump is applied to the upstream reservoir 10.

As time elapses, the variation (decay) of the pressure pulse P occurs at the upper and downstream reservoirs 10 and 20. After finding a curve representing the variation of the pressure pulse by the upper stream pressure gauge 80 and lower stream pressure gauge 70, the curve is inversely calculated to find the hydraulic conductivity and the specific storativity of the rock sample 100.

The hydraulic conductivity and the specific storativity of the rock sample 100 are found through a curve fitting scheme for a measured value and a theoretical value instead of being directly measured from the variation curve of the pressure. In addition, when the least difference is made between the measured value and theoretical value, two estimated parameters are set as parameters of the corresponding rock sample 100.

Theoretical variation curve of the pressures $p_u$ and $p_d$ at the upstream reservoir and the downstream reservoir may be obtained through following Equation 1.

$$\frac{p_u}{P} = \frac{1}{1+\alpha+\alpha\beta} + 2\sum_{m=1}^{\infty} \frac{(\cos\phi_m - \beta\phi_m\sin\phi_m)\exp(-\phi_m^2\tau)}{(1+\alpha+\alpha\beta-\beta\phi_m^2)\cos\phi_m - \phi_m(1+\alpha\beta+2\beta)\sin\phi_m}$$

$$\frac{p_d}{P} = \frac{1}{1+\alpha+\alpha\beta} + 2\sum_{m=1}^{\infty} \frac{\exp(-\phi_m^2\tau)}{(1+\alpha+\alpha\beta-\beta\phi_m^2)\cos\phi_m - \phi_m(1+\alpha\beta+2\beta)\sin\phi_m}$$

Equation 1

In Equation 1, normalization is performed with respect to the pulse pressure P.

In this case, $\alpha=S_s AL/S_u$, $\beta=S_d/S_s AL$, and $\tau=kt/(S_s L)$.

In the above equation, A and L represent the cross sectional area and the length of the sample, respectively, $S_u$ and $S_d$ represent compressive storage constants at the upper and downstream reservoirs, respectively, $S_s$ represents a specific storativity, k represents hydraulic conductivity, t represents time from a time point at which a pulse is generated, and $\Phi m$ is a solution of following Equation 2.

$$\tan\phi = \frac{(1+\alpha\beta)\phi}{\beta\phi^2 - \alpha}$$

Equation 2

Figure 2:
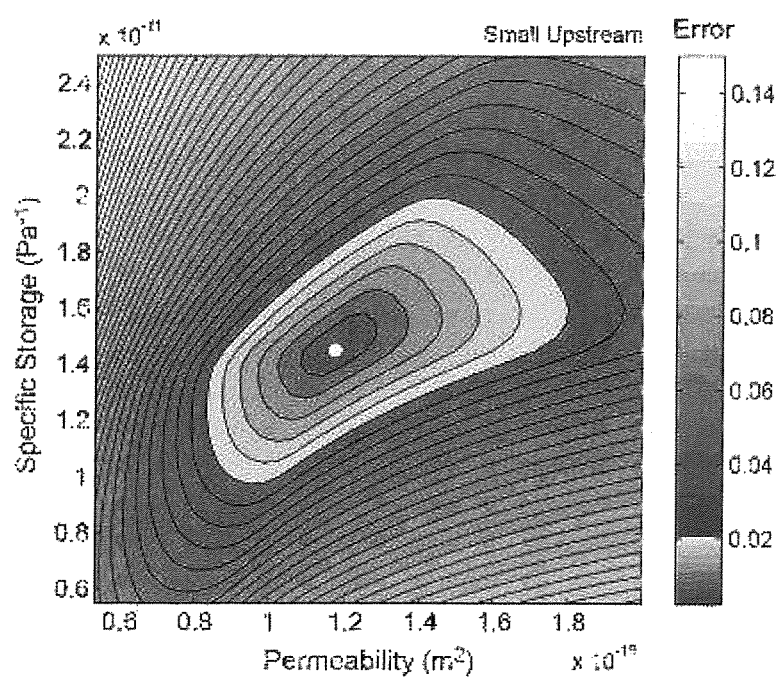
FIG. 2 is a view showing the graph of an objective function and a related measurement error, in which the measurement error represents the ratio with the pressure pulse intensity.
Figure 3:
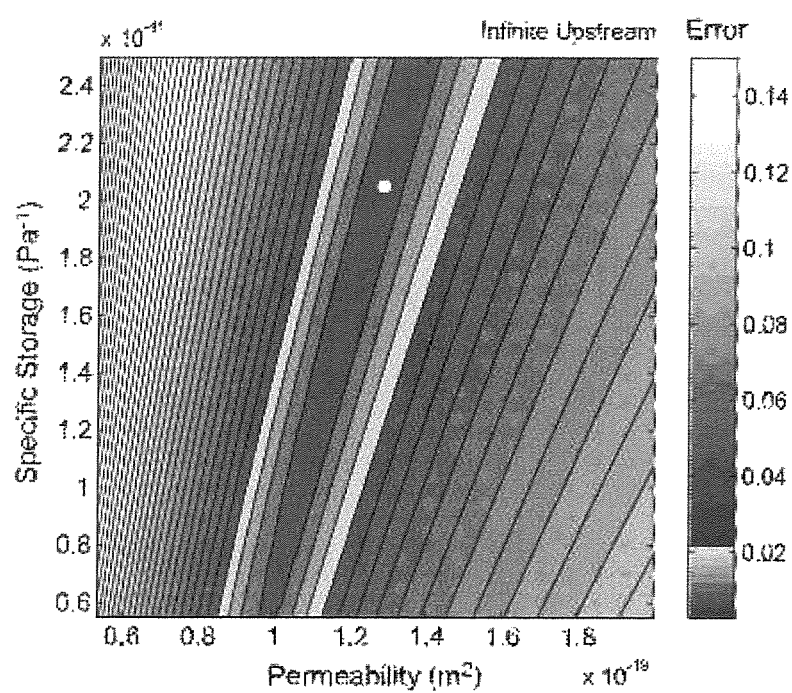
FIG. 3 is a view showing a graph of objective functions affected by each other and related measurement errors.

The sum (or an average value) of differences between calculation values obtained through the above calculation and measurement values obtained from the hydraulic test according to the present invention is referred to as an objective function, and the objective function may be expressed as a function of the hydraulic conductivity, which is represented in a horizontal axis, and specific storativity which is represented in a vertical axis as shown in FIGS. 2 and 3.

After calculating the objective function in the range of the hydraulic conductivity and the specific storativity including the minimum values of the objective function, coordinate values (minimum values) are obtained from a contour when the objective function represents the least values, and set as the hydraulic conductivity and the specific storativity which are measurement values of the rock sample 100.

The value of the objective function is increased in a direction away from the coordinates representing the least values. In this case, the value of the objective function represents an error of a pressure measurement value.

The error is represented in the form of a bar graph at the right side of FIG. 2.

In this case, as the measurement error is increased, that is, the measurement error goes toward the upper side of the bar graph representing the error, the uncertainty of each parameter is increased.

When the graph of the objective function is used, the uncertainty of the hydraulic conductivity and the specific storativity can be found.

In detail, when the average value of the measurement error is 2% of the pressure pulse in FIG. 2, the average value of the measurement error may be expressed in a light gray color at the center of the graph of the objective function.

In this case, the uncertainty of the hydraulic conductivity (permeability) is in the range of about −20% to 60%, and the uncertainty of the specific storativity (specific storage) is in the range of −30% to 60%.

Summarizing the description made with reference to FIG. 2 in brief, according to one constitution of the present invention, in the state that the axial pressure and the confining pressure are applied to the rock sample, and the upper and downstream reservoirs are connected with the rock sample, the hydraulic conductivity and the specific storativity are obtained through a pressure pulse-decay measurement scheme to apply a pressure pulse from an outside and marked in horizontal and vertical axes of the graph of the objective function. Then, coordinate values representing the minimum values of the contour are obtained from the graph of the objective function in which the hydraulic conductivity and the specific storativity are marked in the horizontal and vertical axes of the graph thereof, and set as the hydraulic conductivity and the specific storativity of the rock sample.

FIG. 3 is a graph showing an objective function representing mutually-affected uncertainties.

In FIG. 3, the uncertainties are mutually affected. As shown in FIG. 3, a contour representing experimental errors has an oval shape which is slightly inclined.

When comparing with the case in which the uncertainty of one of parameters is generally known, the case, in which the uncertainty of one of the parameters is not known, significantly increases the uncertainty of another parameter.

For example, when the uncertainty of the specific storativity is 0, the uncertainty of the hydraulic conductivity is approximately 20%. However, when the uncertainty of the specific storativity is unknown, the uncertainty of the hydraulic conductivity is significantly increased.

In this case, when the objective functions of FIGS. 2 and 3 are overlapped with each other, the uncertainty of the specific storativity is restricted. Accordingly, the uncertainty of the hydraulic conductivity is significantly restricted, so that the uncertainties of two parameters may be reduced.

The details thereof will be described with reference to FIG. 4.

In order to obtain a graph formed by overlapping the objective functions of FIGS. 2 and 3, at least two experiments having different boundary conditions are required.

To this end, the sizes of the upstream reservoir 10 are differently adjusted by using two valves 90 and 95 provided at the upstream reservoir 10 of the 3-axis-core holder device 500 shown in FIG. 1, and experiments are repeated several times under mutually different boundary conditions. Thereafter, if the experimental results are analyzed by overlapping the experimental results, the uncertainty can be significantly reduced.

In other words, a series of experiments having different boundary conditions are performed several times, the uncertainties of the experiments are overlapped, and a common set of the uncertainties is expressed. Then, the uncertainty can be significantly reduced when comparing with one experiment.

Accordingly, as shown in FIG. 3, the uncertainty of one parameter can be restricted by another experiment even in the experiment in which uncertainties are mutually affected. Accordingly, the measurement uncertainty of the whole system can be reduced.

Figure 4:
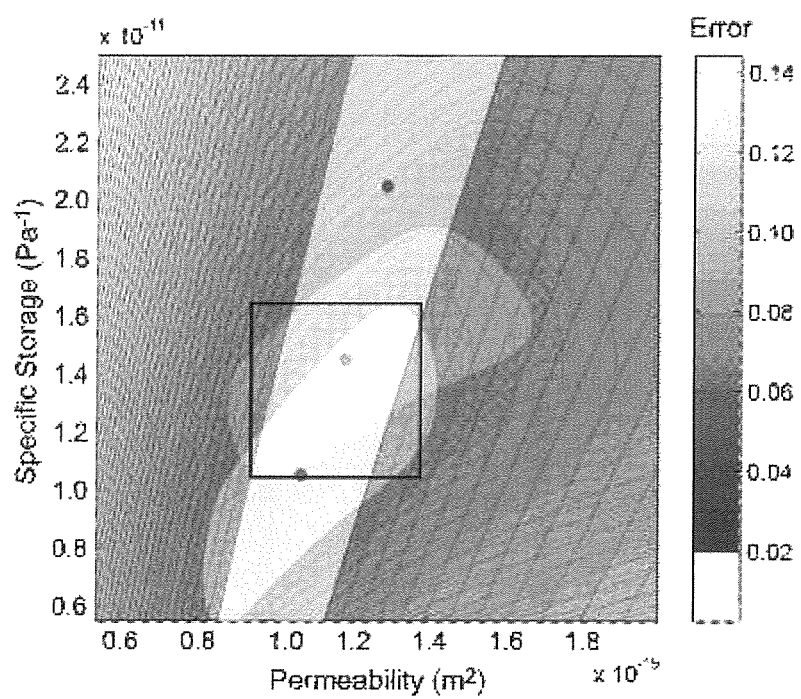
FIG. 4 is a view showing the uncertainties of the hydraulic conductivity and the specific storativity in the graph of the objective function when objective functions obtained through total three hydraulic tests are overlapped with each other.

As shown in FIG. 4, when objective functions obtained from total three hydraulic tests are overlapped with each other, the uncertainties of the hydraulic conductivity and the specific storativity are expressed in the shape of a rectangle at the center of a graph of the objective functions. In this case, it can be understood that the uncertainty can be significantly reduced when comparing with the case that only one hydraulic test result is used.

Summarizing the description made with reference to FIGS. 3 and 4 in brief, according to another constitution of the present invention, graphs of objective functions obtained by repeating the pressure pulse-decay measurement while changing boundary conditions are overlapped with each other and a common set of the graphs is expressed, thereby significantly reducing the uncertainty of the hydraulic conductivity and the specific storativity of the rock sample.

Although a method of reducing uncertainty in pressure pulse-decay measurement according to the exemplary embodiments of the present invention have been described for the illustrative purpose, it is understood that the present invention should not be limited to these exemplary embodiments but various changes, modifications, equivalents can be made by one ordinary skilled in the art within the spirit and scope of the present invention as hereinafter claimed.

What is claimed is:

1. A method of reducing an uncertainty in pressure pulse-decay measurement, the method comprising:
   placing a rock sample inside a sleeve in housing;
   fixing the rock sample by mounting end plugs and porous disks on left and right sides of the rock sample, respectively;
   connecting upstream and downstream reservoirs to the porous disks of the fixed rock sample axially outward of the porous disks;
   attaching pressure gauges to the upper and downstream reservoirs, respectively;
   applying an axial pressure and a confining pressure to the rock sample placed in the sleeve to form a closed pressure system;
   applying a pressure pulse to the rock sample in the closed pressure system through the upstream reservoir; and
   finding a hydraulic conductivity and a specific storativity of the rock sample,
   wherein the finding of the hydraulic conductivity and the specific storativity comprises obtaining coordinates representing minimum values of a contour in a graph of an objective function, the objective function representing a sum or an average value of differences between calculated values of the hydraulic conductivity and the specific storativity based on one or more theoretical equations and variation measurement values of the pressure pulse obtained from the pressure gauges when the pressure pulse is decayed; and
   setting the minimum values as the hydraulic conductivity and the specific storativity of the rock sample.

2. The method of claim 1, wherein the sleeve comprises a rubber.

3. The method of claim 1, wherein the applying of the axial pressure and the confining pressure to the rock sample comprises supplying a fluid to a fluid inflow space.

4. The method of claim 3, wherein the fluid comprises oil.

5. A method of reducing an uncertainty in pressure pulse-decay measurement, the method comprising:
   placing a rock sample inside a sleeve in a housing;
   fixing the rock sample by mounting end plugs and porous disks on left and right sides of the rock sample, respectively;
   connecting upstream and downstream reservoirs to the fixed rock sample;
   attaching pressure gauges to the upper and lower reservoirs, respectively;
   placing two valves, which are spaced apart from each other, to adjust a size of the upstream reservoir;
   applying an axial pressure and a confining pressure to the rock sample placed in the sleeve to form a closed pressure system;
   applying a pressure pulse to the rock sample in the closed pressure system through the upper reservoir; and
   finding a hydraulic conductivity and a specific storativity of the rock sample,
   wherein the finding of the hydraulic conductivity and the specific storativity comprises obtaining coordinates representing minimum values of a contour in a graph of an objective function, the objective function representing a sum or an average value of differences between calculated values of the hydraulic conductivity and the specific storativity based on one or more theoretical equations and variation measurement values of the pressure pulse obtained from the pressure gauges when the pressure pulse is decayed; and
   setting the minimum values as the hydraulic conductivity and the specific storativity of the rock sample.

6. The method of claim 5, wherein the sleeve comprises a rubber.

7. The method of claim 5, wherein the applying of the pressure pulse comprises applying the pressure pulse through the upstream reservoir in a state that the size of the upstream reservoir is adjusted by controlling the two valves spaced apart from each other.

8. The method of claim 7, wherein uncertainties of the hydraulic conductivity and the specific storativity of the rock sample are reduced by expressing graphs of objective functions obtained by repeating the applying of the pressure pulse several times through overlap of the graphs.

9. The method of claim 5, wherein the applying of the axial pressure and the confining pressure to the rock sample comprises supplying a fluid to a fluid inflow space.

10. The method of claim 9, wherein the fluid comprises oil.

* * * * *